United States Patent [19]

Hala

[11] Patent Number: 6,026,348
[45] Date of Patent: Feb. 15, 2000

[54] APPARATUS AND METHOD FOR COMPRESSING MEASUREMENT DATA CORRELATIVE TO MACHINE STATUS

[75] Inventor: Roger A. Hala, Minden, Nev.

[73] Assignee: Bently Nevada Corporation, Minden, Nev.

[21] Appl. No.: 08/949,905

[22] Filed: Oct. 14, 1997

[51] Int. Cl.$^7$ ..................................................... G01H 11/06
[52] U.S. Cl. ............................... 702/56; 702/33; 702/54; 702/126; 702/183; 73/659
[58] Field of Search .................................. 702/56, 32–34, 702/38, 41–44, 54, 70–72, 76, 77, 79, 103–106, 124, 113–115, 126, 141, 180, 183–187, 189–191, 193–195, 198, FOR 123–FOR 126, FOR 135, FOR 136, FOR 168, FOR 171, 35; 364/474.16, 474.17, 474.19, 728.03, 178, 179, 528.14, 528.15; 324/76.13, 76.15, 76.22, 76.33; 340/683, 870.16, 679, 680; 73/583, 579, 116, 659, 660, 570, 577, 578, 66, 582, 618, 457, 462, 1.14, 778, DIG. 1; 704/205, 500, 501, 503, 504, 203, 224, 229

[56] References Cited

U.S. PATENT DOCUMENTS

| | | | |
|---|---|---|---|
| Re. 31,750 | 11/1984 | Morrow | 702/34 |
| 2,763,840 | 9/1956 | Pfleger | 333/17.1 |
| 3,462,555 | 8/1969 | Presti | 704/205 |
| 3,471,648 | 10/1969 | Miller | 704/224 |
| 3,620,069 | 11/1971 | Cole, Jr. | 73/583 |
| 3,641,550 | 2/1972 | Lynas et al. | 73/583 |
| 3,681,530 | 8/1972 | Manley et al. | 704/203 |
| 3,742,395 | 6/1973 | Yoneyama | 333/17.1 |
| 3,758,758 | 9/1973 | Games et al. | 702/56 |
| 3,936,611 | 2/1976 | Poole | 704/503 |
| 3,959,592 | 5/1976 | Ehrat | 380/28 |
| 4,081,749 | 3/1978 | Peterson | 370/297 |
| 4,157,457 | 6/1979 | Sakoe et al. | 704/205 |
| 4,408,285 | 10/1983 | Sisson et al. | 702/56 |
| 4,480,480 | 11/1984 | Scott et al. | 73/769 |
| 4,488,240 | 12/1984 | Kapadia et al. | 702/56 |
| 4,553,213 | 11/1985 | Hyatt | 332/185 |
| 4,590,466 | 5/1986 | Wiklund et al. | 340/870.28 |
| 4,621,263 | 11/1986 | Takenaka et al. | 340/870.07 |
| 4,908,785 | 3/1990 | Cubbins et al. | 73/583 |
| 5,303,346 | 4/1994 | Fesseler et al. | 704/230 |
| 5,309,149 | 5/1994 | Bozeman, Jr. | 340/683 |
| 5,311,561 | 5/1994 | Akagiri | 375/240 |
| 5,365,787 | 11/1994 | Hernandez et al. | 73/660 |
| 5,394,349 | 2/1995 | Eddy | 364/725.02 |
| 5,426,665 | 6/1995 | Cleverly et al. | 375/200 |
| 5,430,241 | 7/1995 | Furuhashi et al. | 84/603 |
| 5,453,945 | 9/1995 | Tucker et al. | 364/725.01 |
| 5,485,160 | 1/1996 | Suganuma | 342/195 |
| 5,502,650 | 3/1996 | Naruse et al. | 73/659 |
| 5,519,166 | 5/1996 | Furuhashi et al. | 84/603 |
| 5,519,645 | 5/1996 | Bohley | 704/205 |
| 5,544,073 | 8/1996 | Piety et al. | 364/528.14 |
| 5,602,749 | 2/1997 | Vosburgh | 364/474.16 |

*Primary Examiner*—Hal Wachsman
*Attorney, Agent, or Firm*—Dennis DeBoo

[57] ABSTRACT

A method and apparatus for compressing, storing and transmitting measurement data correlative to machine status is disclosed in which the measurement data is continuously sensed, sampled and processed to extract significant spectral elements including magnitude and phase information from each successive period of the originally measured data and to store those spectral elements in a memory means from an initial period of significant spectral elements and each successive period of significant spectral elements which have changed since the previous period for developing a compressed data history correlative to a continuous history of the status of the machine being monitored and from which continuous signals can be regenerated and analyzed for any earlier historical time.

46 Claims, 9 Drawing Sheets

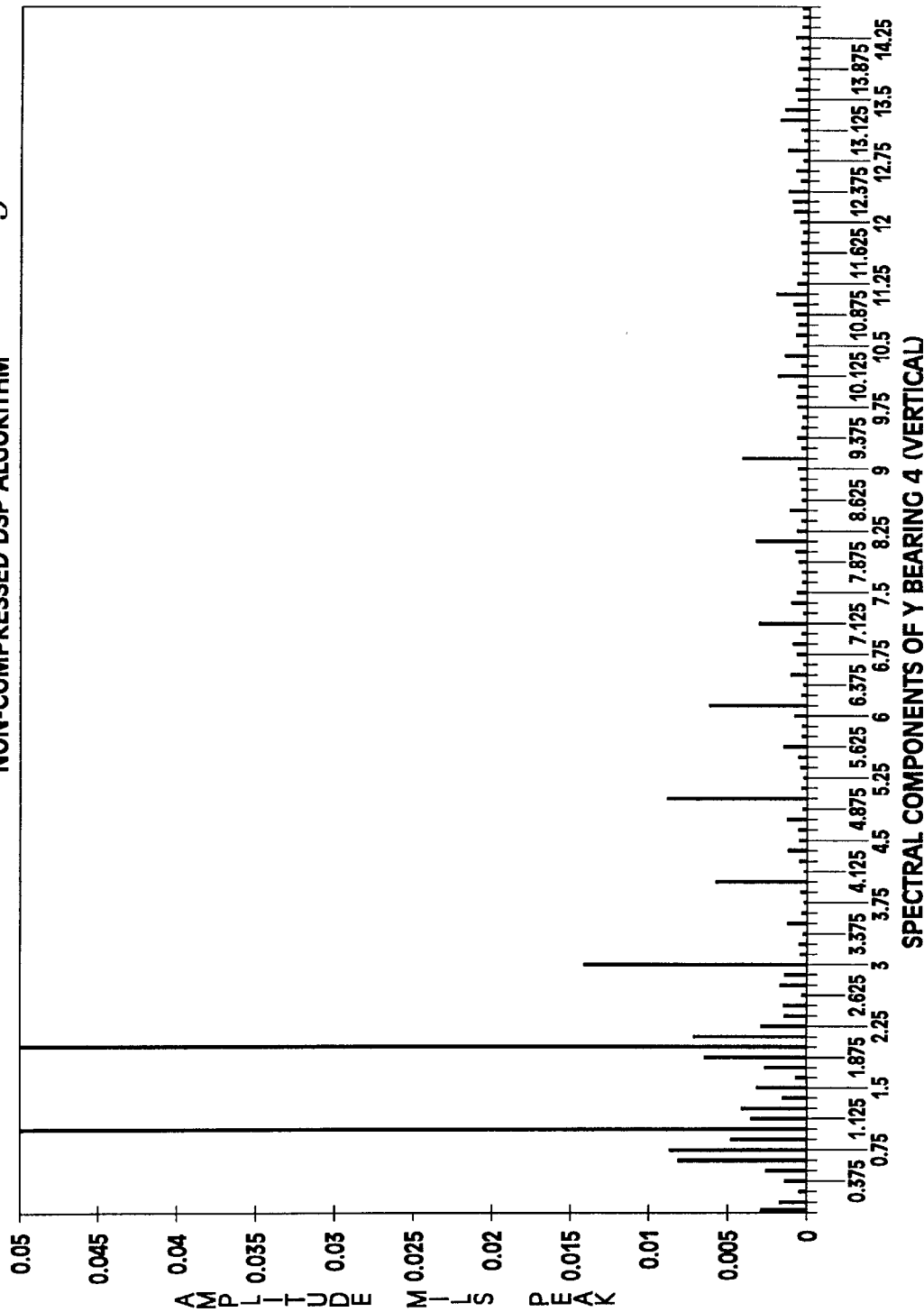

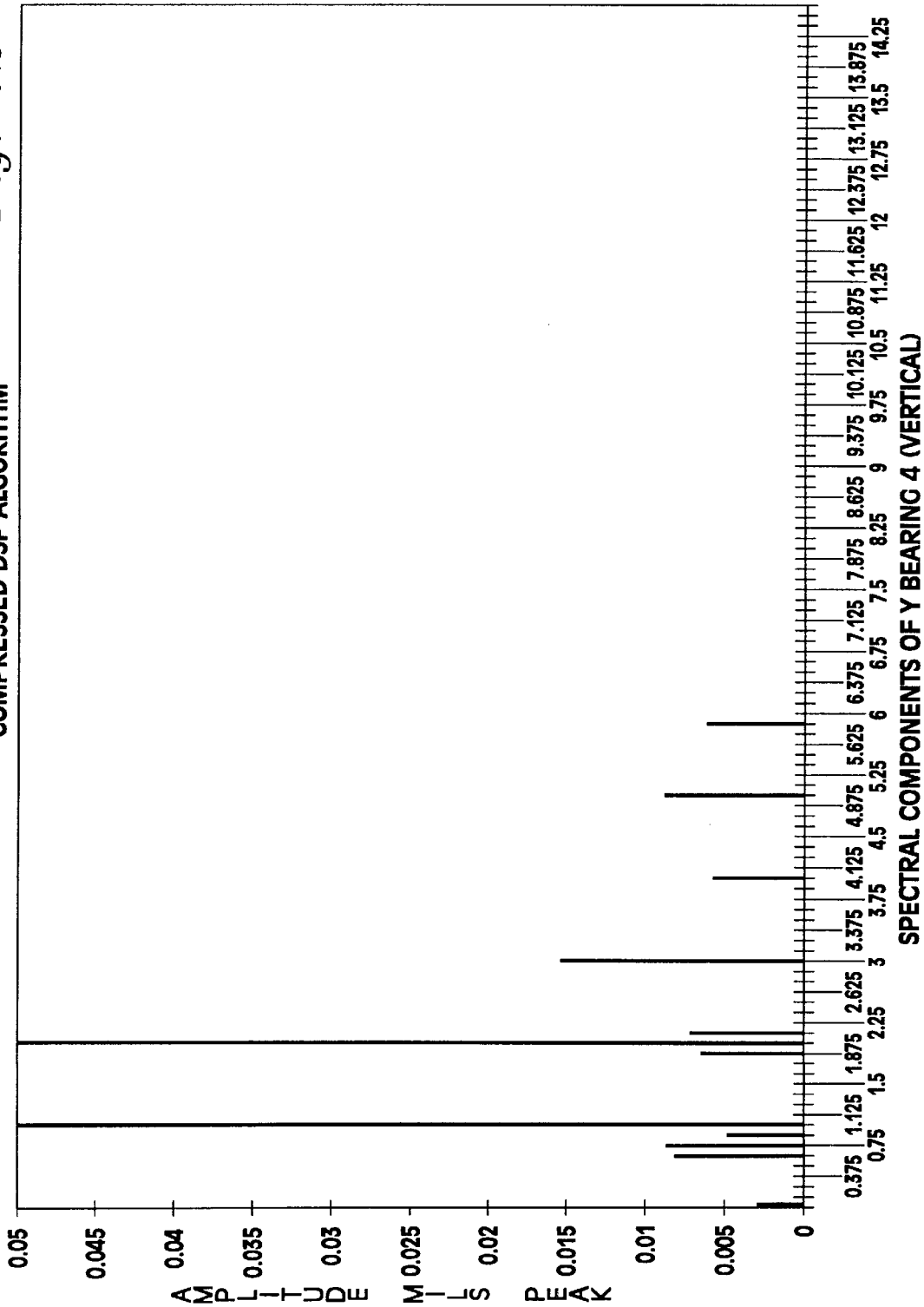

APPARATUS AND METHOD FOR COMPRESSING MEASUREMENT DATA CORRELATIVE TO MACHINE STATUS

FIELD OF THE INVENTION

The present invention relates generally to a method and apparatus for compressing measurement data correlative to machine status, and in particular, to a method and apparatus for compressing machine vibration data to allow significant compression of the original data for storage and transmission wherein the compressed data can be retrieved and reconstructed to provide a complete continuous waveshape history of machine performance.

BACKGROUND OF THE INVENTION

Machinery monitoring systems have been permanently installed in, inter alia, today's large process plants, power generation stations and pipelines in an attempt to provide machinery protection by continuously monitoring the behavior and performance characteristics of machinery at a multiplicity of points and possibly acquiring data from these points simultaneously. More recently, the trend has been to enhance the monitoring systems by directly interfacing computers to the systems for periodically collecting data from these systems for historical trend, machinery diagnostics and predictive maintenance purposes. However, these current systems use methods which only retain a small history of machine performance at best.

For example, current systems periodically collect, store, display and print machinery data in a variety of formats using a variety of schemes. One such scheme is to continuously sample and store data at a high sample rate to obtain data with relatively high data time resolution, and as storage space fills, to replace the stored data with a new data set. This scheme does not automatically store the historical information necessary to analyze one or more problems, may not represent a long enough period of time to represent the on-set of one or more problems and does not readily identify the occurrence of one or more problems.

Another scheme is to intermittently capture data "snapshots" of the machine performance. A small set of "snapshots" are maintained in memory and saved in the event of a machine problem. However, the time represented by the "snapshots" may not be adequate to represent historical machine performance or may not represent a continuous set of data with the machine fault occurring between data sets previously stored in memory.

A common scheme is to represent the machine performance with an overall magnitude, eliminating all of the details that are contained to generate the magnitude. Although the magnitude can be used for protection, it does little to identify the causes of the problem.

The disadvantage of these schemes is they either consume too much memory, may not provide a rapid method to identify when one or more problems commence and to describe its progress or may lose the ability to diagnose one or more problems after the fact by either destroying the data with replacement information, or by taking data samples with the data of interest falling between the samples.

Therefore, if one were to continuously capture the machine data using current techniques, the memory requirements of such data storage can be enormous considering that the data is preferably collected over a period of months or years. In addition, long transmission times are required for transmitting large quantities of continuous machine data to a remote data base for permanent storage and with enough detail and history to perform fault analysis and diagnosis.

In addition, with current systems it is a challenge to capture and store infrequently occurring machine anomalies and to ensure that these anomalous events get managed using past learning experiences and procedures according to historical data. For example, the cause of and the procedures needed to deal with these machine anomalies may not be repetitive enough to stay within peoples' memory. Further, to make matters worse, many anomalous events occur so infrequently that people who managed and learned from previous situations have either changed jobs or are not available by the time a similar anomalous event occurs again. These anomalous events can have a profound impact if not managed correctly. For example, improper management of one of these anomalous events may cause loss of life, loss of property, fugitive emissions and other undesirable consequences.

Therefore, what is needed is a system which, inter alia, allows machine data to be compressed and stored in a reduced form which represents a continuous set of data correlative to a continuous history of machine performance without allowing machine faults between data sets to go undetected and thus unrepresentable. In addition, a need exists for a system which reduces data volume sufficiently to allow transmission using commonly available transmission media. Furthermore, a need exists for a system which allows stored compressed data to be retrieved and reconstructed to provide a complete continuous waveshape history of machine performance. Moreover, a system is needed which provides continuous data acquisition for diagnostic and predictive maintenance purposes for maximizing the machine's life while minimizing its cost and averting any catastrophic events when in operation.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
| --- | --- | --- |
| 2,763,840 | September 18, 1956 | K. W. Pfleger |
| 3,462,555 | August 19, 1969 | A. J. Presti |
| 3,471,648 | October 7, 1969 | R. L. Miller |
| 3,620,069 | November 16, 1971 | A. Cole, Jr. |
| 3,641,550 | February 8, 1972 | Lynas, et al. |
| 3,681,530 | August 1, 1972 | Manley, et al. |
| 3,742,395 | June 26, 1973 | Yoneyama |
| 3,758,758 | September 11, 1973 | Games, et al. |
| 3,936,611 | February 3, 1976 | Poole |
| 3,959,592 | May 25, 1976 | Ehrat |
| 4,081,749 | March 28, 1978 | Peterson |
| 4,157,457 | June 5, 1979 | Sakoe, et al. |
| 4,408,285 | October 4, 1983 | Sisson, et al. |
| 4,480,480 | November 6, 1984 | Scott, et al. |
| Re. 31,750 | November 27, 1984 | Morrow |
| 4,488,240 | December 11, 1984 | Kapadia, et al. |
| 4,553,213 | November 12, 1985 | Hyatt |
| 4,590,466 | May 20, 1986 | Wiklund, et al. |
| 4,621,263 | November 4, 1986 | Takenaka, et al. |
| 5,303,346 | April 12, 1994 | Fesseler, et al. |
| 5,309,149 | May 3, 1994 | Bozeman, Jr. |
| 5,311,561 | May 10, 1994 | Akagiri |
| 5,394,349 | February 28, 1995 | Eddy |

-continued

| PATENT NO. | ISSUE DATE | INVENTOR |
| --- | --- | --- |
| 5,426,665 | June 20, 1995 | Cleverly, et al. |
| 5,430,241 | July 4, 1995 | Furuhashi, et al. |
| 5,453,945 | September 26, 1995 | Tucker, et al. |
| 5,485,160 | January 16, 1996 | Suganuma |
| 5,519,166 | May 21, 1996 | Furuhashi, et al. |
| 5,544,073 | August 6, 1996 | Piety, et al. |
| 5,602,749 | February 11, 1997 | Vosburgh |

The patent to Cubbins, et al., U.S. Pat. No. 4,908,785 issued Mar. 13, 1990, teaches the use of a data compression method for telemetry of vibration data. The method achieves compression by filtering the incoming signal to extract a low frequency band. This low frequency band is sent to a multiplexed system without encryption or compression but can be sampled at a lower frequency since the upper frequency has been significantly reduced. The total range of frequencies is then divided, either by fractional octave filters, DFT or FFT to amplitude detect bands of frequencies and then the magnitude of the signals in this band or bands are extracted. These magnitudes are multiplexed with the lower frequency signals to give an overall or specific distribution of energy. Once processed, the low frequency data can be extracted but a waveshape can not be generated from the information present.

The other prior art listed above but not specifically described further catalog the prior art of which the applicant is aware. These references diverge even more starkly from the references specifically distinguished above.

SUMMARY OF THE INVENTION

The present invention is distinguished over the known prior art in a multiplicity of ways. For one thing, the present invention provides a system for compressing, storing and transmitting raw dynamic machine data in a reduced form which can be retrieved and reconstructed into a continuous set of data correlative to a continuous waveshape history of machine performance without allowing machine faults between data sets to go undetected and thus unrepresentable. In addition, the present invention reduces data volume sufficiently to allow transmission using commonly available transmission media by, inter alia, retaining only significant data and by eliminating data created from noise sources. Furthermore, the present invention provides a system which continuously collects and stores information on machine performance to generate a historical data base which captures, inter alia, infrequently occurring machine anomalies and allows historical dynamic machine performance data to be retrieved and reconstructed including machine phase information. The system also allows a rule set to be generated from the historical data which is an accurate assessment of these anomalous events. The present invention further provides a system which allows access to the data base at any time so that past learned machine performance can be used. Moreover, the present invention provides a system which, inter alia, provides continuous life time data acquisition for diagnostic and predictive maintenance purposes for maximizing the machines life while minimizing its cost and averting any catastrophic events when in operation.

In one preferred form, the system of the present invention includes a computational means operatively coupled to a sampling means and to at least one machine, for example, to at least one bearing or measurement point to be monitored. The system is adapted to receive signals from a plurality of sensors operatively coupled to the machine. Preferably, the sampling means is operatively coupled to and receives data from at least one sensor sensing raw dynamic machine vibration signals correlative to machine status. Preferably, the computational means incorporates a timing pulse into commands given to the sampling means for synchronously sampling the raw dynamic machine vibration signals into discrete digital values. Alternatively, the computational means can issue commands to the sampling means for sampling the raw dynamic machine vibration signals into discrete digital values asynchronously with machine speed. These discrete digital values are transmitted to the computational means and are processed in sets according to the present invention.

The computational means performs a fast fourier transform analysis on a first data set of digital values to preferably transform the data into a series of spectral elements including both amplitude and phase information. The spectral elements are compared to a dominate criteria and those which pass this criteria are stored in a memory means along with a unique identifying tag. The identifying tag preferably tags each spectral element with an element number and a real time value identifying a time in history when the corresponding instantaneous value of the raw vibration signal was captured from the vibration sensor. The spectral elements of the first data set which have passed the dominate criteria can be transmitted to and stored in, for example, the host computer along with at least one unique identifying tag associating an element number and real-time value to each transmitted spectral element.

The computational means transforms a subsequent set of digital values into a subsequent series of spectral elements which are compared to the dominate criteria and those which pass are stored in the memory means and compared to the first set of spectral elements which have been previously stored in the memory means for determining any anomalous behavior between the two. Only those elements included in the subsequent series which are anomalous, because they differ by a comparison criteria from the first set of spectral elements are stored in the memory means. In addition, the anomalous spectral elements in the subsequent series can be are transmitted to and stored in the host computer along with at least one unique identifying tag associating an element number and a real-time value to each transmitted spectral element.

The computational means transforms each further subsequent set of digital values into further subsequent series of spectral elements which are each compared to the dominate criteria and those which pass are compared to the previous set of spectral elements which have been stored in the memory means for determining any anomalous behavior between subsequent sets. Only those elements included in each further subsequent series which are anomalous are stored in the memory means and can be transmitted to and stored in the host computer along with at least one unique identifying tag associating an element number and a real-time value to each transmitted spectral element. In addition, information regarding the sample rate of the raw vibration signals is stored in the memory means and transmitted to and stored in the host computer.

The data is preferably transmitted to and stored in the host computer as a spectral frequency element number, in phase and quadrature magnitudes and/or amplitude and phase elements and a real time reference. The spectral frequency is preferably related to shaft speed or time. After receipt of the data, the host computer can perform an inverse fourier transform to regenerate a continuous waveshape from the significant spectral content for any given time in history.

For example, the computer can recreate a continuous waveshape at any given time by using the anomalous spectral elements representing performance for that time. These are accessed by sequencing backwards through the stored spectral element sets to identify and use only those elements whose magnitudes are found to have significance at the desired point in time. These elements will have been identified to have a significant magnitude and/or phase prior to the desired point in time and will exist to a time later than the desired point. The combination of all elements which fit this existence criteria will be included to construct the waveshape. Thus, a continuous waveshape history of machine status at any given time may only require a few anomalous spectral elements to be stored for that given time. Therefore, the present invention provides a significant improvement in data compression, the consumption of memory to store this data and the time needed to transmit this data to a remote location.

The compression method of this invention is a lossy technique and thus, once the data is compressed the original signal cannot be recreated exactly. However, the compression technique of the present invention is highly effective because it only retains the significant content of the data and it preferable only stores the data if it has changed from previously stored data.

OBJECTS OF THE INVENTION

An object of the present invention is to provide a new, novel and useful apparatus and method for compressing measurement data correlative to machine status.

A further object of the present invention is to provide an apparatus and method as characterized above which collects measurement data at a predetermined mode and samples the data input over a number of input cycles and transforms the data using a fast fourier transform method.

Another further object of the present invention is to provide an apparatus and method as characterized above for compressing, storing and transmitting raw dynamic machine data in a reduced form.

Another further object of the present invention is to provide an apparatus and method as characterized above which reduces data volume sufficiently to allow transmission using commonly available transmission media by retaining only significant data.

Another further object of the present invention is to provide an apparatus and method as characterized above which reduces data volume by eliminating data created by noise sources in the system.

Another further object of the present invention is to provide an apparatus and method as characterized above which allows historical dynamic machine performance data to be retrieved and reconstructed including machine phase information.

Another further object of the present invention is to provide an apparatus and method as characterized above for providing a continuous set of data correlative to a continuous history of machine performance without allowing machine faults between data sets to go undetected and thus unrepresentable.

Another further object of the present invention is to provide an apparatus and method as characterized above which continuously collects and stores information on machine performance to generate a historical data base which captures, inter alia, infrequently occurring machine anomalies.

Another further object of the present invention is to provide an apparatus and method as characterized above which allows access to the data at any time so that past learned machine performance can be used.

Another further object of the present invention is to provide an apparatus and method as characterized above which provides continuous lifetime data acquisition for diagnostic and predictive maintenance purposes.

Viewed from a first vantage point, it is an object of the present invention to provide a signal processing method for processing machinery signals correlative to machine status, the steps including: sensing signals correlative to machine status; converting said signals into digital values; storing a series of said digital values into packets; comparing a subsequent packet of said digital values with one said stored packet of said digital values; storing only said digital values included in said subsequent packet which are anomalous because they differ by a criteria from comparable digital values of said previously stored packet of said digital values; transmitting a signal correlative to said packet of digital values and to the subsequent packets including flagging anomalous data in said subsequent packets of digital values.

Viewed from a second vantage point, it is an object of the present invention to provide a machine vibration signal processing method, the steps including: sampling a vibration signal; subjecting said vibration signal to a transformation means for transforming said vibration signal into a series of spectral elements; comparing said series of spectral elements against a criteria for retention and storing in a memory means said spectral elements which pass said criteria; sampling a subsequent vibration signal; subjecting said subsequent vibration signal to said transformation means for transforming said subsequent vibration signal into a subsequent series of spectral elements; comparing said subsequent series of spectral elements to said criteria for retention and then comparing said subsequent series of spectral elements which have passed said criteria for retention with said previously stored series of spectral elements; storing in said memory means spectral elements of said subsequent series which have passed said criteria for retention and which differ from said spectral elements of said previous series by a pre-determined amount.

Viewed from a third vantage point, it is an object of the present invention to provide an apparatus for compressing data correlative to continuous machine vibrations signals, comprising, in combination: at least one sensor operatively coupled to a machine for sensing machine vibration in the form of continuous electrical signals; sampling means adapted to receive from said sensor continuous electrical signals and to converting into digital values said electrical signals; a control circuit commanding said sampling means to convert said electrical signals into digital values; means for uniquely tagging each digital value with each command by said control circuit including a real time value for identifying a time in history of when the corresponding instantaneous value of the continuous electrical signal was captured; means for storing in a memory means a periodicity of said digital values; means for comparing at least one said periodicity of said digital values with a subsequent periodicity of said digital values to determine anomalous digital values, and means for storing in said memory means said anomalous digital values of said subsequent periodicity of said digital values which have changed from said previous periodicity of said digital values.

Viewed from a fourth vantage point, it is an object of the present invention to provide a machine vibration signal processing method, the steps including: sampling continuous vibration signals from a machine; transforming said vibration signals into discrete digital values; storing at least one packet of digital values in a memory means and storing a marker in said memory means for identifying the position and the time of capture of each digital value; comparing a subsequent packet of digital values with at least one said packet of digital values; storing digital values of said subsequent packet of digital values which differ from at least one said packet of digital values and storing markers for identifying the position and time of capture of each differing value; comparing further subsequent packets of digital values with previously stored packets of digital values; storing digital values of said further subsequent packets of digital values which differ from said previously stored values and storing markers in said memory means identifying the position and time of capture of each differing value; reconstituting any packet of digital values into a continuous wave form from the values stored for said packet and from the values of previous packets which correspond to the missing values of said packet being reconstituted.

Viewed from a fifth vantage point, it is an object of the present invention to provide a signal compression method for storing historical data correlative to devolving machine status, the steps including: sensing signals correlative to machine status; sampling said signals; transforming said sampled signals into a series of spectral elements defining a first reading; determining dominate spectral components of a periodicity of said series of spectral elements based on a pre-determined criteria; storing said periodicity of dominate spectral components; determining dominate spectral components of a subsequent periodicity of said series of spectral elements based on said pre-determined criteria; comparing said subsequent periodicity of dominant spectral components with said previously stored periodicity of dominant spectral components to ascertain devolvement in respect of spectral components correlative to machine status; transmitting to and storing in a host computer said spectral components of said subsequent periodicity which change from said spectral components of said previously stored spectral components and when the changes occur; defaulting to resensing in the absence of devolvement; generating a continuous signal correlative to a continuous signal in which said subsequent periodicity of dominant spectral components was produced from by transforming said stored components of said subsequent periodicity and said stored components of said previous periodicity which fails to differ from said subsequent periodicity of dominant spectral components.

Viewed from a sixth vantage point, it is an object of the present invention to provide a method for compressing data from waveforms characterizing machine vibration, the steps including: successively producing a series of samples representing generally instantaneous values of a series of waveforms at time-spaced intervals; transforming a first period of said samples of a first waveform included in said series of waveforms into a first series of spectral elements storing only those elements in said first series of spectral elements which are significant based on a predetermined criteria; transforming said series of samples of each subsequent waveform included in said series of waveforms into a subsequent series of spectral elements; successively storing only those elements in each said subsequent series which have changed since the last stored elements in said series of spectral elements.

Viewed from a eighth vantage point, it is an object of the present invention to provide a method for compressing measurement data correlative to machine status, the steps including: sensing machine data correlative to machine status; sampling said data; transforming said sampled data into spectral elements; comparing said spectral elements to a user definable criteria for retention; storing in a memory means those spectral elements which have passed said user definable criteria for retention wherein said stored elements are correlative to machine status.

Viewed from a eighth vantage point, it is an object of the present invention to provide a method for compressing measurement data correlative to machine status, the steps including: continuously sensing cyclic machine vibration from at least one machine in the form of electrical signals correlative to machine status; sensing at least one mechanical phase reference mark on a rotating shaft of at least the one machine; relating the mechanical phase reference mark of the rotating shaft to the electrical signals of machine vibration wherein the mechanical angle defines intervals of electrical signals; sampling the machine vibration electrical signals under the orchestration of a control signal; transforming said sampled signals into spectral elements; converting said spectral elements into amplitude and phase elements; comparing both the magnitude and phase of each subsequent interval of elements with a previous interval of elements to determine if the amplitude and/or phase of each subsequent element has changed more than a user definable amount from the element of a previous interval; communicating the changed element values to a remote site for storage.

Viewed from a ninth vantage point, it is an object of the present invention to provide a device for compressing measurement data correlative to machine status, said device comprising in combination: at least one sensor operatively coupled to a machine for sensing data correlative to machine status; sampling means operatively coupled to at least said one sensor for sampling said sensed data into discrete elements; processor means operatively coupled to said sampling means for transforming said discrete elements into spectral elements and converting said spectral elements into magnitude and phase elements; means for defining intervals of magnitude and phase elements; means for storing a current interval of magnitude and phase elements; means for comparing a subsequent interval of magnitude and phase elements with said current interval of magnitude and phase elements; means for storing only said elements from said subsequent interval which are anomalous because they differ by a criteria from comparable elements of said current interval of elements wherein compressed measurement data correlative to machine status is continuously captured.

These and other objects will be made manifest when considering the following detailed specification when taken in conjunction with the appended drawing figures.

BRIEF DESCRIPTION OF THE DRAWINGS

FIGS. 11 and 12 respectively show uncompressed and compressed spectrum plots of the signals S and S' respectively shown in FIGS. 9 and 10.

DESCRIPTION OF PREFERRED EMBODIMENTS

Figure 1:
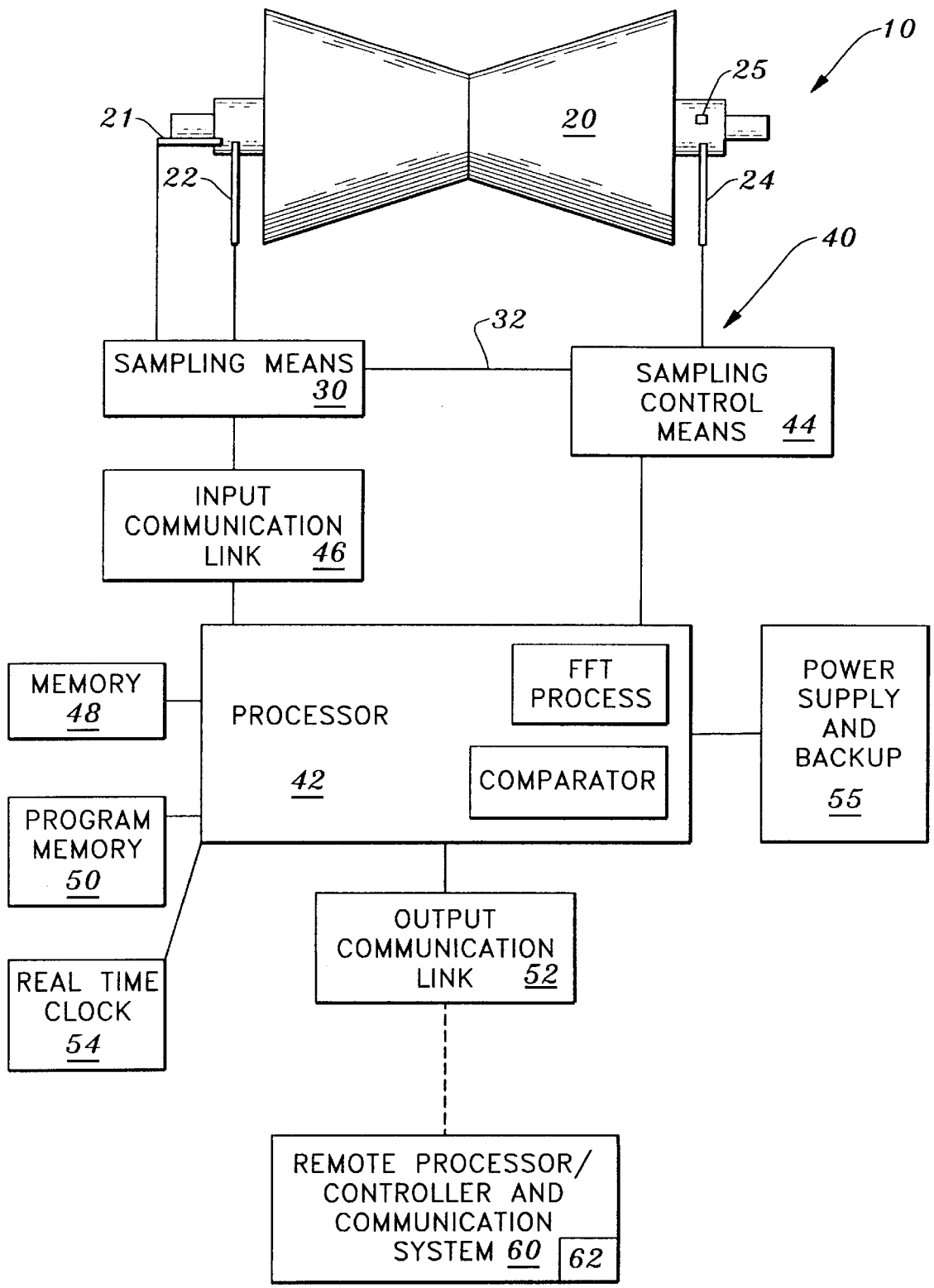
FIG. 1 is a diagrammatic view of a system according to the present invention.

Considering the drawings, wherein like reference numerals denote like parts throughout the various drawing figures, reference numeral 10 is directed to the system according to the present invention.

In essence, and referring to FIG. 1, the system 10 includes a computational means 40 operatively coupled to a sampling means 30 and a host computer or a remote processor/controller and communication system 60. The sampling means 30 is operatively coupled to at least one sensor 22 which in turn is removable or rigidly coupled to a machine 20 for sensing raw dynamic machine data correlative to machine status. The sampling means 30 is adapted to receive and sample the dynamic machine data under the orchestration of the computational means 40. The sampled data is communicated to the computational means 40 which transforms periods of sampled data into a periods of spectral elements while continuously collecting samples from the sampling means 30. At the outset, a first period of sampled data is transformed into a first period of spectral elements which are compared to a criteria and those which pass this criteria are stored in a memory means 48 along with at least one unique identifying tag associating an element number and a real-time valve of occurrence to each stored spectral element. In addition, the first period of spectral elements can be transmitted to and stored in a host computer 60 along with at least one unique identifying tag associating an element number and a real-time valve to each transmitted spectral element.

The computational means 40 receives and transforms each subsequent period of sampled data into subsequent periods of spectral elements which are in turn compared to the dominate criteria and those which pass are compared to the previous period of spectral elements which have been previously stored in the memory means for determining any anomalous behavior between the two. Preferably, only those elements included in each subsequent period which are anomalous are used to replace the corresponding data in the previous period of spectral elements for creating a new period used for comparing further subsequent periods. In addition, only those elements included in each subsequent period which are anomalous with respect to the previous period are transmitted to and stored in the host computer 60 along with at least one unique identifying tag associating an element number and a real-time valve to each transmitted spectral element.

The host computer 60 can then recreate a continuous waveshape correlative to the original raw dynamic machine data at any given time in history by, for example, using the anomalous spectral elements stored for that time and sequencing backward through the stored spectral elements sets to capture and use only those elements which have a different element number then the anomalous spectral elements and which are needed to form the original dominant spectral content. Therefore, the system 10 provides a significant improvement in data compression, the consumption of memory needed to store data for extended periods of time and the time needed to transmit this data to the remote host computer 60.

Figure 2:
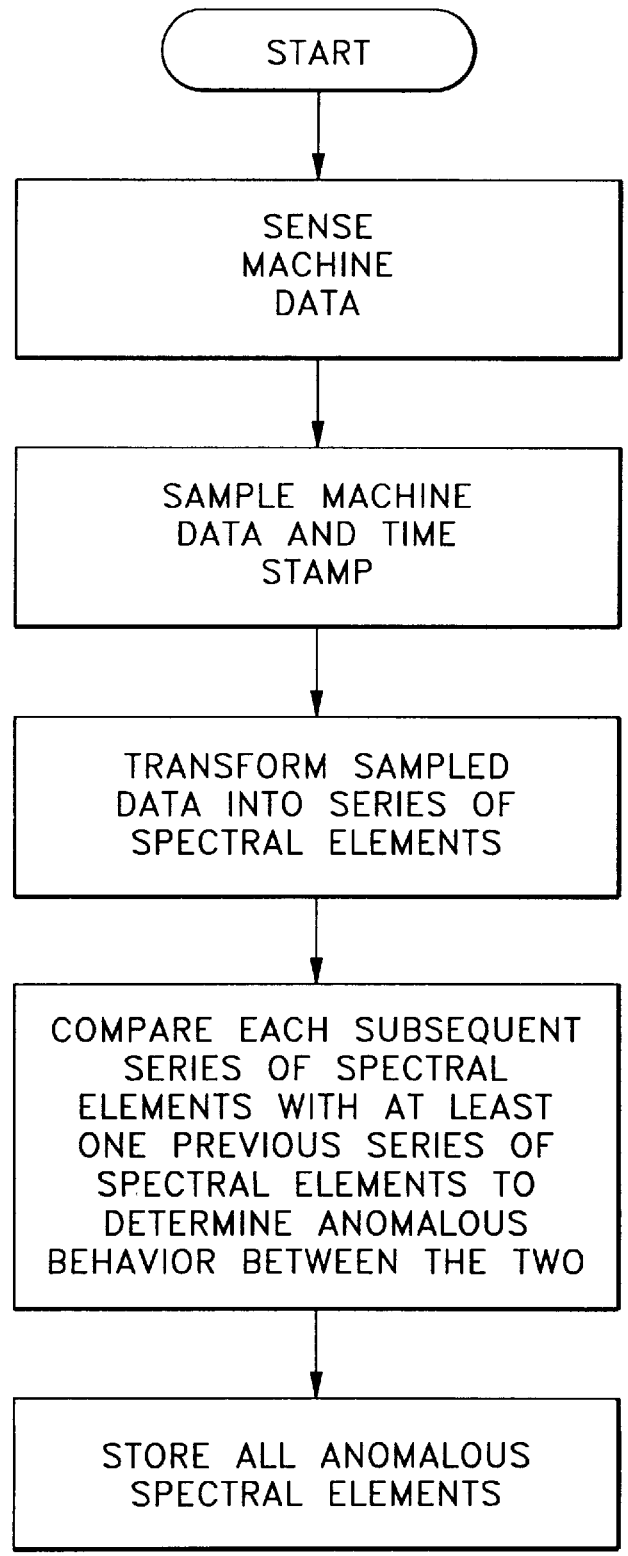
FIG. 2 is a general block diagram of a method according to the present invention.

More specifically, and referring to FIGS. 1 and 2, the system 10 is operatively coupled to at least one vibration sensor 22. The vibration sensor 22 is coupled to the machine 20 for monitoring the vibration of a machine casing, a rotating member or other structural motion associated with the machine 20. The vibration as seen by the vibration sensor 22 is related to the energy in the system imparted by the rotating element or other structural motion of the machine and is modified by the constraints of the other mechanical elements of the machine 20. The output of the vibration sensor 22 is a continuous electrical representation of the motion or the rate of change of the motion of the machine 20. The system 10 could also employ a plurality of sensors to operate independently or simultaneously to monitor the status of the machine 20.

In addition to at least the one vibration sensor 22 a phase sensor 24 is preferably operatively coupled to the machine 20 for sensing a mechanical phase reference mark 25 on, for example, a rotating shaft of the machine 20. This mark 25 is preferably used to relate the mechanical angle of the rotating shaft to the electrical signals of the sensor 22. For example, and referring to FIG. 9, the electrical signals S outputted by the sensor 22 (and/or sensor 21) can be marked with a point P each time the reference 25 is sensed by the sensor 24 which, in this example, is once per revolution of the shaft. Thus, creating a mechanical (zero degree) phase reference mark used to relate the mechanical angle of the rotating shaft to the electrical signal S outputted by the sensor 22 and to a correlative signal S' reconstructed from compressed electrical signals S (please see FIG. 10). The electrical signals from the phase sensor 24 are input to a sampling control circuit 44 which will be delineated infra.

The sampling means 30 is operatively coupled to the sensor 22 and is adapted to receive the electrical signals from the sensor 22. The sampling means 30 converts the signals into digital values at intervals established by the sampling control means 44 instigating a sample through a control line 32. The sampling control means preferably includes means for providing both synchronous and asynchronous timing pulses and specifically, synchronous and asynchronous timing pulses correlative with respect to machine speed. The output of the sampling means 30 is a series of digital values representing the instantaneous value of the sensed electrical signals at the time the control line 32 instigates the sampling of the sensed electrical signals outputted by the sensor 22. A typical embodiment of the sampling means 30 is an analog to digital converter.

The computational system 40 includes a processor 42, including a digital signal processor means, operatively coupled to the sampling means 30 via a input communication interface 46 for receiving the series of digital values representing the raw vibration machine data sensed by the sensor 22. The sampling control means 44 is operatively coupled to and interposed between said sampling means 30 and said processor 42 for controlling the sampling rate of sampling means 30. The computational system 40 further includes the memory means 48, a program storage means 50, an output communication interface 52 and a real time clock 54. The computational system 40 employs the real time clock 54 for uniquely tagging each digital value with a real time value for identifying a time in history of when the corresponding instantaneous value of the signal was captured from the sensor 22 and can also be used to provide a real time value for identifying sampling rates of the sampling means 30. Processor 42 further includes a fast fourier transform algorithm (FFT) which can be stored in the program memory 50. Generally, and referring to FIG. 2, the FFT algorithm transforms a first set of digital values into a first series of spectral elements while the processor 42 continuously collects digital samples from the sampling means 30. A subsequent set of digital values is transformed into a subsequent series of spectral elements which are compared to the first set of spectral elements which have been stored in memory means 48. The processor 42 includes means for comparing the first series of spectral elements with the subsequent series of spectral elements and determining any anomalous behavior between the two and/or comparing the first series and subsequent series of spectral elements with a user definable criteria. The computational system 40 further includes an output communication interface 52 operatively coupled between the processor 42 and the host computer 60 for transmitting the anomalous digital values to the host computer 60 where, for example, they are stored in a historical data base 62. The output communication interface 52 can take the form of, inter alia, wire, fiber optics, networks, radio frequency (RF) links, internet links, microwave links and satellite links. In addition, since the data is preferably time tagged it can be sent in brief bursts from a collection site (computational system 40) to a remote site (host computer 60) and then reconstituted.

Preferably, the sampling control means 44 has two modes. The first mode issues electrical commands to the sampling means 30 from the sampling control means 44 to sample the vibration signal in discrete time increments which can be controlled by the processor 42. In this mode each sample is spaced apart by a pre-determined amount of time. For machine management with an upper frequency of interest of 20 kilohertz, data collection can take 20 milliseconds (1024 samples at a 51.2 kilo sample/second rate).

In a second mode the samples are taken at discrete phase increments. A typical phase increment of 11.25 degrees results in data collection in no less than 32 milliseconds (1024 samples taken 32 samples each revolution of the shaft to a maximum speed of 60,000 RPM). These signals are preferably generated by taken the period of the once per turn phase reference signal generated by the phase sensor 24, dividing by the number of samples per revolution and causing a sample signal from the sampling control means 44 to the sampling control line 32 at this shorter period.

Figure 3:
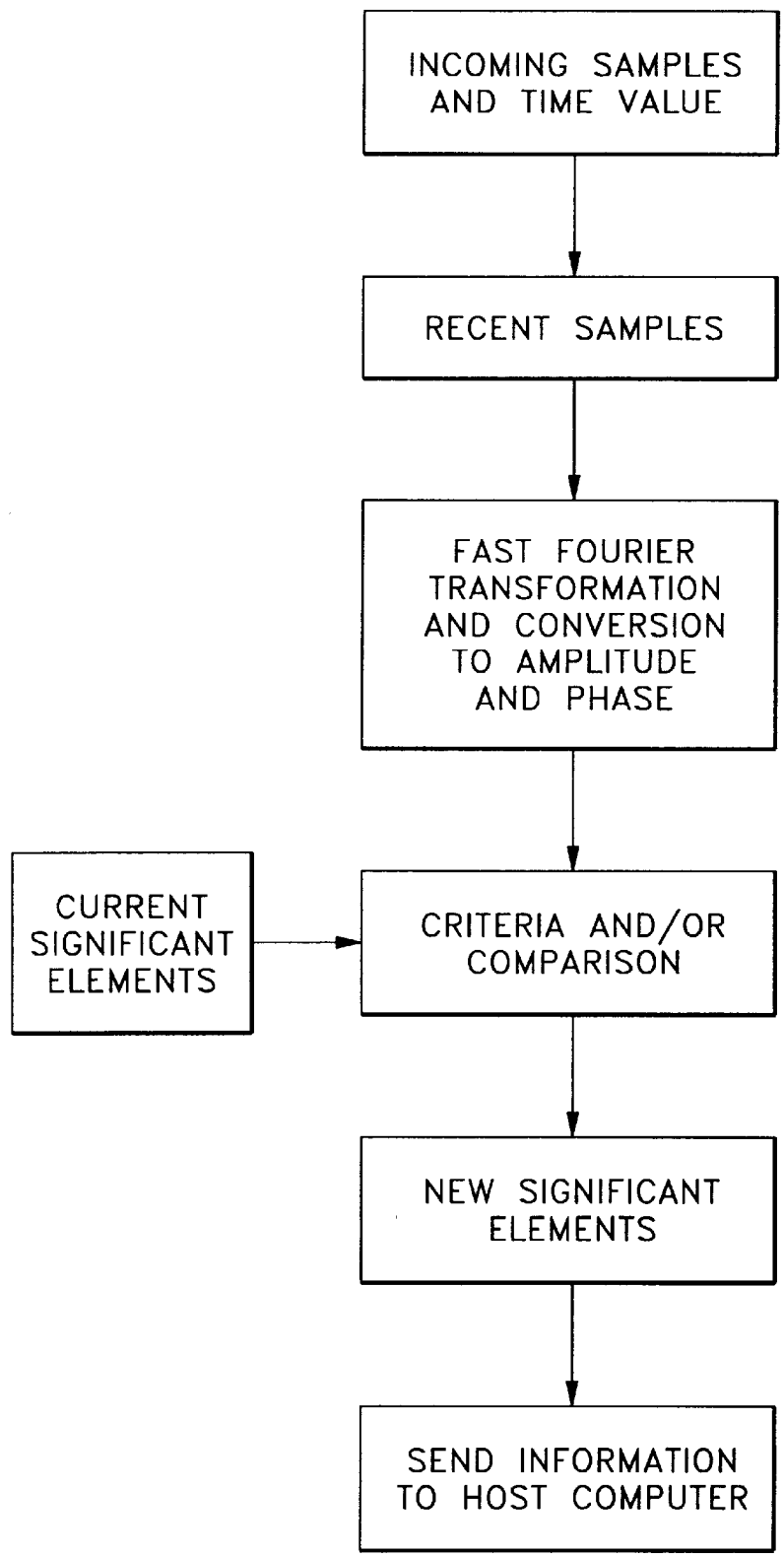
FIG. 3 is a block diagram detailing a method of compressing measurement data correlative to machine status according to the present invention.
Figure 4:
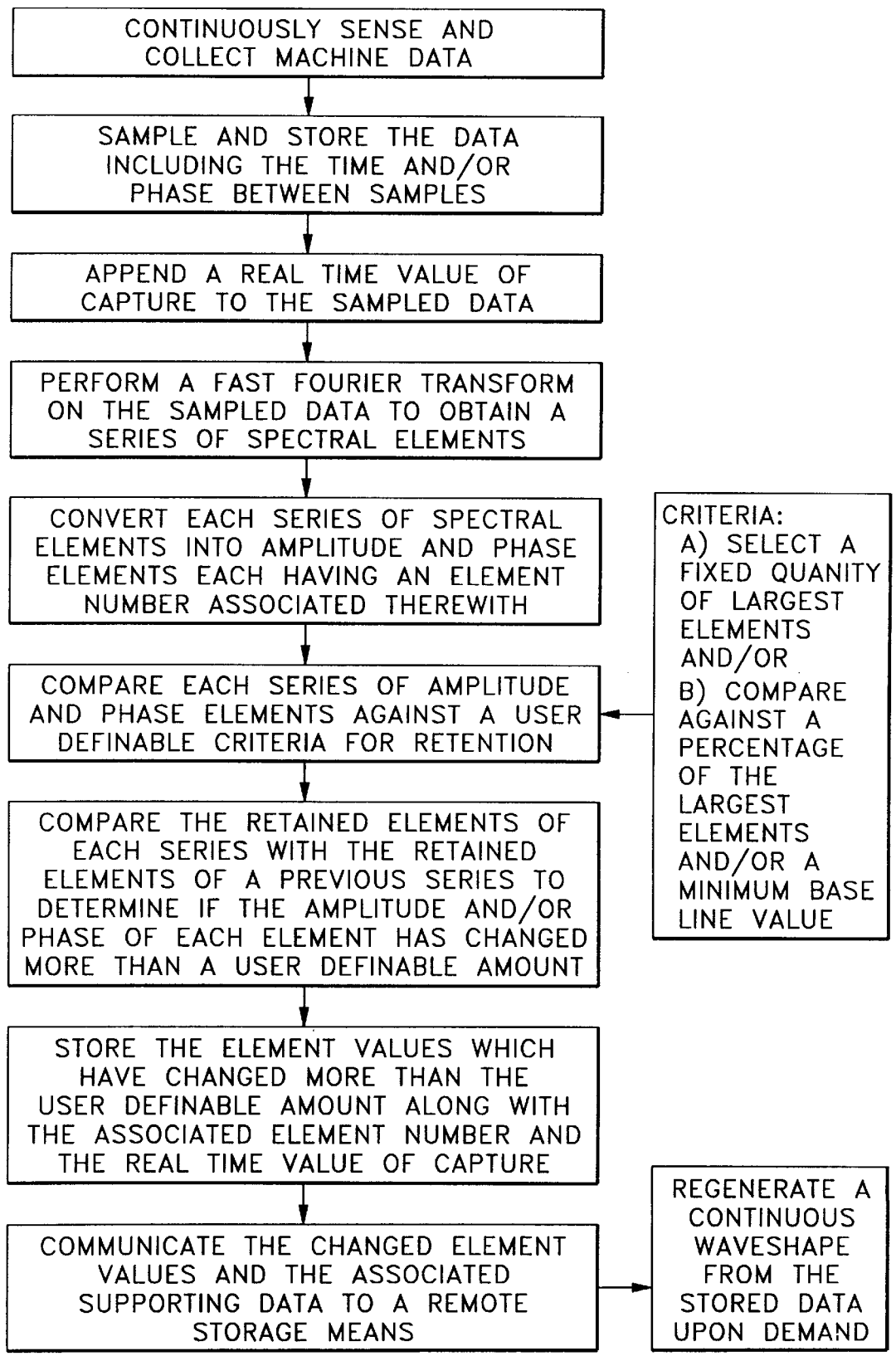
FIG. 4 is a block diagram specifically a method of compressing measurement data correlative to machine status according to the present invention.

Still more specifically, and referring to FIGS. 1, 2 and 3 the system 10 performs a series of operations on the incoming digital stream of vibration data samples transmitted from the sampling means 30 to the processor 42. The incoming digital stream of vibration data samples are temporarily stored in memory 48 along with the sampling rate or the real time value or phase representing the time or phase between adjacent samples. After a first set of samples is gathered, the set is processed by the processor 42 using a fast fourier transform algorithm. Simultaneously, digital data samples continue to be collected while processing is conducted on the first set of data and subsequent sets of data. Each sampled data set which is processed by the processor 42 results in a data set of spectral elements representing the sine and cosine convolution of the data. The elements in each data set are then preferably converted to amplitude and phase elements. Thus, both amplitude and phase data is available for future comparison and ultimately signal reconstruction.

Furthermore, at least one unique identifying tag associating an element number and a real-time valve of occurrence is associated with each spectral element. The unique real time value can be obtained from the real time clock 52 and is used, inter alia, to identify the real time in which the data was captured. Typically, this time can be collected with a resolution of one millisecond.

In a highly cyclic input, the significant information is contained in dominant spectral components, with the lower amplitude and non-harmonic components resulting from discontinuities due to electrical sampling, electrical noise or mechanical or electrical run out sensed by the vibration sensor.

The criteria for determining dominant spectral components of any element or series of elements can be based on a user definable criteria. The user definable criteria includes using a fixed number of spectral lines, using a minimum level above which values are dominant, using a level related to the highest spectral line or any combination of these criteria. Thus, the present invention simultaneously reduces data volume and eliminates noise. Preferably, compression is realized by only transmitting and saving the spectral lines that have changed by an established percentage or value since the last reporting to the host computer and when these changes occurred. Thus, the host computer 60 can regenerate continuous waveshapes from the dominant spectral content for any given time by performing an inverse fourier transform and displaying the resultant waveshapes on a computer display.

Specifically, the determination of the dominant spectral content of each set of the spectral elements is accomplished by using a user definable criteria for retention. This criteria can be applied in a number of different ways. One preferable method is to select a fixed quantity of the largest elements. These dominant elements are compared against the dominant elements determined in a previous fast fourier transform computation. If the magnitude or phase of a single element has changed more than a user definable number picked for the percentage change, then the new element value is stored in memory and the element number and time is noted for transmission to the host computer 60. All the elements that do not fall in the quantity of the largest elements are ignored.

Alternatively, a second preferred method for the criteria for retention retains the element if the element is greater than a fixed percentage of the largest element and/or greater than a base line element magnitude. Any element which is larger than a user definable percentage of the largest element is retained as long as it is larger than a minimum value. It has been discovered that as the signal approaches zero, noise values predominate (i.e. white noise or a flat spectral distribution). Thus, the minimum element magnitude is selected to be slightly larger than the noise spectral amplitudes and if they are less than the noise spectral amplitude they are discarded. Note that in this method, the number of elements that qualify for retention can vary.

The last operation is to communicate those elements to the host computer which have passed the selection criteria. If no elements have changed sufficiently to meet the criteria to notify the host than no transmission takes place and the host knows that the values which are presently held for subsequent elements are valid for the elements for that time as well. If only one element of a larger number has changed than it is the only one reported to the host computer as having been changed.

The output communication interface communicates the changed elements to the host computer 60. The transmission data includes a sample time, an element number and a real time value for each element and the corresponding magnitude and phase of each element. This data may be sent in any format.

Once the host computer is provided with the elements of the fourier transform, it can recreate the values of the sampled sets using an inverse fourier transform. For example, if we know the content of the elements of the vibration at any time we can recreate the waveshape at that time.

In summary, the present invention makes it possible to take continuous sample data sensed from a running machine, perform a fourier transform and collect and store only those elements which are significant and only those elements which changed since the last stored values. In addition, the present invention makes it possible to reconstruct continuous signal at any time by also storing the time that the value changed and information regarding the sample rate of the signal. Furthermore, the compression method of the present invention is a lossy technique and thus, once the data is compressed the original signal cannot be recreated exactly. However, the compression technique of the present invention is highly effective because it only retains the significant content of the data and it only stores the data if it has changed.

In use and in operation, the system 10 is operatively coupled to at least one sensor 22 and as shown in FIG. 1, the system is operatively coupled to orthogonally disposed sensors 21 and 22 which in turn are removable or rigidly coupled to the machine 20 for sensing raw dynamic machine vibration signals correlative to machine status. The sensor 22 and/or 21 may take the form of, inter alia, a displacement (proximity) transducer, a velocity transducer and/or an acceleration transducer. In addition, the system 10 is preferably coupled to at least one timing transducer 24 for collecting a timing pulse correlative to, for example, a once per shaft revolution. The timing sensor 24 may take the form of, inter alia, a proximity probe which observes a physical gap change event, an optical pick up which observes a change in wave reflectivity event or a magnetic pick up.

The system 10 collects the raw vibration signals on a continuous basis from at least the one vibration sensor 22 and transmits the vibration signals to the sampling means 30 for sampling the vibration signals into discrete samples. Simultaneously, the system 10 collects a timing pulse from the timing sensor 24 for providing a measurement of shaft rotative speed and a reference point for measuring phase angle for relating a mechanical angle of the rotating shaft to the vibration signals of at least the one vibration sensor 22. In one preferred embodiment the timing sensor 24 transmits the timing pulse to the sampling control means 44. The sampling control means 44 incorporates the timing pulse into commands which are issued to the sampling means 30 to sample the vibration signals into discrete phase increments. Furthermore, the sampling control means 44, under the control of the processor 42, can issue commands to the sampling means 30 to sample the vibration signals at different sampling rates, sample modes based on elapsed time and/or change in machine speed or frequency span or mechanical phase wherein the data representation can be optimized to identify machine behavior under specific conditions.

The discrete samples from the sampling means 30 are transmitted to the processor 42 via the communication link 48 interposed between and operatively coupled to the sampling means 30 and the processor 42. Simultaneously, the sampling means 30 continues to collect, sample and transfer data from the vibration sensor 22 to the processor 42. Simultaneously, the processor 42 performs a fast fourier transform analysis on the incoming data to transform the data into spectral elements.

Figure 5:
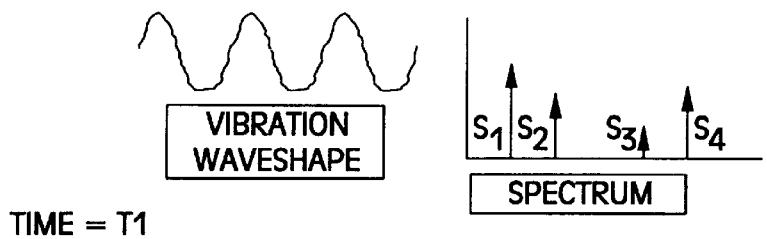
FIGS. 5 through 8 are graphical representations of continuous measurement data and graphical representations of spectrum elements resulting from the transformation of the continuous measurement data.

For example, and referring to FIG. 5, at time T1 a continuous vibration signal is sampled into a first data set of digital values and then transmitted to the processor 42 and transformed into a first series of spectral elements including both amplitude and phase information. The spectral elements are compared to a dominate criteria and those which pass this criteria are stored in the memory means 48 along with a unique identifying tag. FIG. 5 graphically shows that four spectral elements which have passed the dominant criteria and are tagged with a unique identifying tag including an element number and a real time value identifying a time in history when the corresponding instantaneous value of the vibration signal was captured by the vibration sensor 22. These spectral elements, $S_1$ through $S_4$, can then be transmitted to and stored in the host computer 60 along with at least one unique identifying tag associating an element number and a real time value to each transmitted spectral element.

Figure 6:
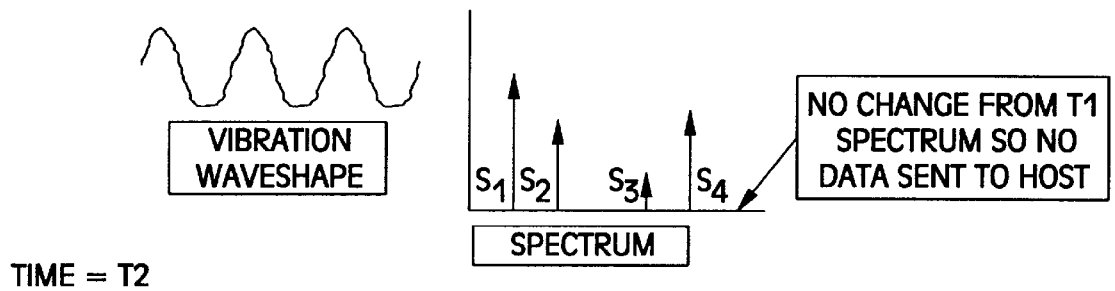

Referring to FIG. 6, at T2 a subsequent continuous vibration signal is sampled into a subsequent set of digital values which are transmitted to the processor 42 and transformed into a subsequent series of spectral elements including both amplitude and phase information. The subsequent series of spectral elements are also compared to the dominant criteria and those which pass are stored in the memory means 48 and compared to the first or previous set of spectral elements which have been previously stored in the memory means for determining any anomalous behavior between the two. Referring to FIG. 6, there is no change in the spectral elements from T1. Therefore the data is preferably not saved in memory means 48 nor is it sent to the host computer 60.

Figure 7:
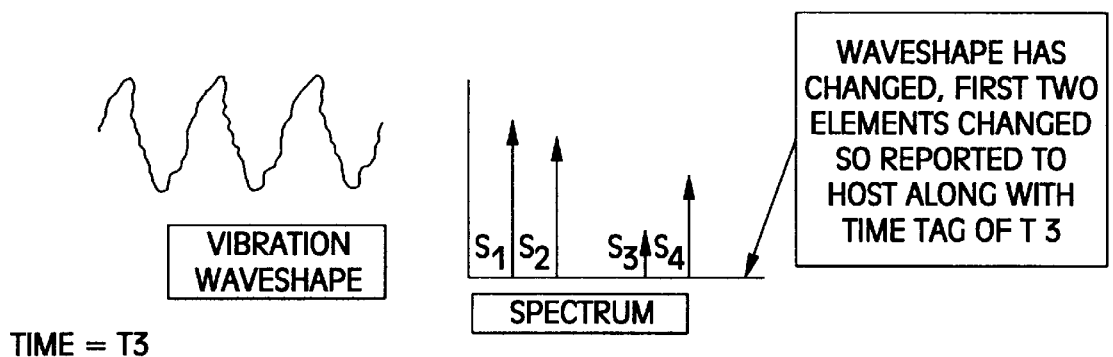

Referring to FIG. 7, at time T3 the vibration waveshape captured from the transducer includes anomalies. Thus, the waveshape has changed and referring to the spectrum plot it can be noted that the first two elements, $S_1$ and $S_2$, are anomalous and thus are stored in memory means 48 and reported to the host computer 60 along with the time tag of T3.

Figure 8:
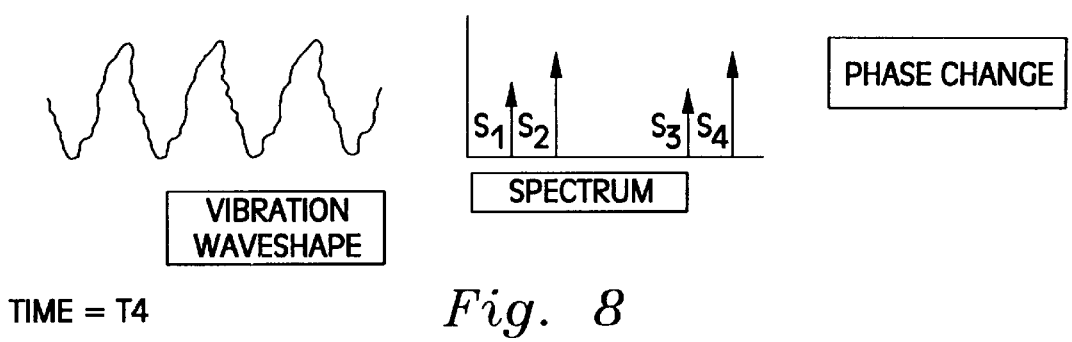

Referring to FIG. 8, at time T4 a phase change of the vibration waveshape has occurred and thus results in two anomalous elements $S_1$ and $S_2$ when compared to the previous set of spectral elements shown in FIG. 7. Thus, the first two elements, $S_1$ and $S_2$, shown in FIG. 8 are stored in memory means 48 and reported to the host computer 60 along with the time tag of T4.

The host computer 60 can recreate a continuous vibration signal at any given time by using the anomalous spectral elements for that time and sequencing backward through the stored spectral element sets to capture and use only those elements which have different element numbers than the anomalous spectral elements and which are needed to form the original dominant spectral content. For example, the computer can re-create the continuous vibration signal shown in FIG. 7 by first sequestering the anomalous spectral elements $S_1$ and $S_2$ shown in FIG. 7 and then sequencing backward and sequestering spectral elements $S_3$ and $S_4$ from the previously stored spectral elements found in the host computer 60. Once the computer has sequestered a given number of spectral elements contained in the original dominant spectral content it may perform an inverse fourier transform analysis to recreate the continuous vibration signal for the given time in history.

Figure 9:
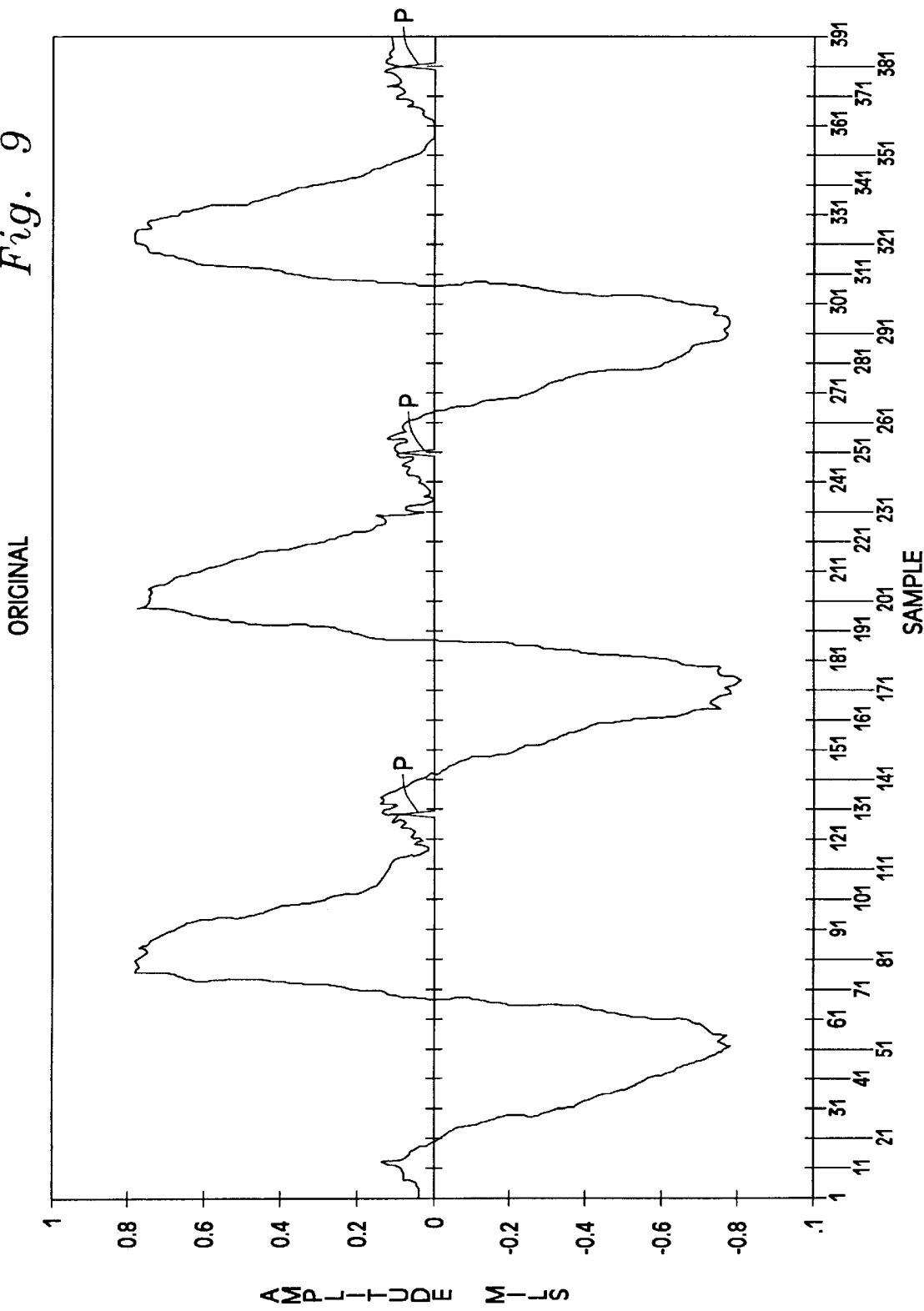
FIG. 9 is a graphical representation of continuous vibration signals sensed by a vibration sensor and mechanical phase reference marks sensed by a mechanical phase sensor.
Figure 10:
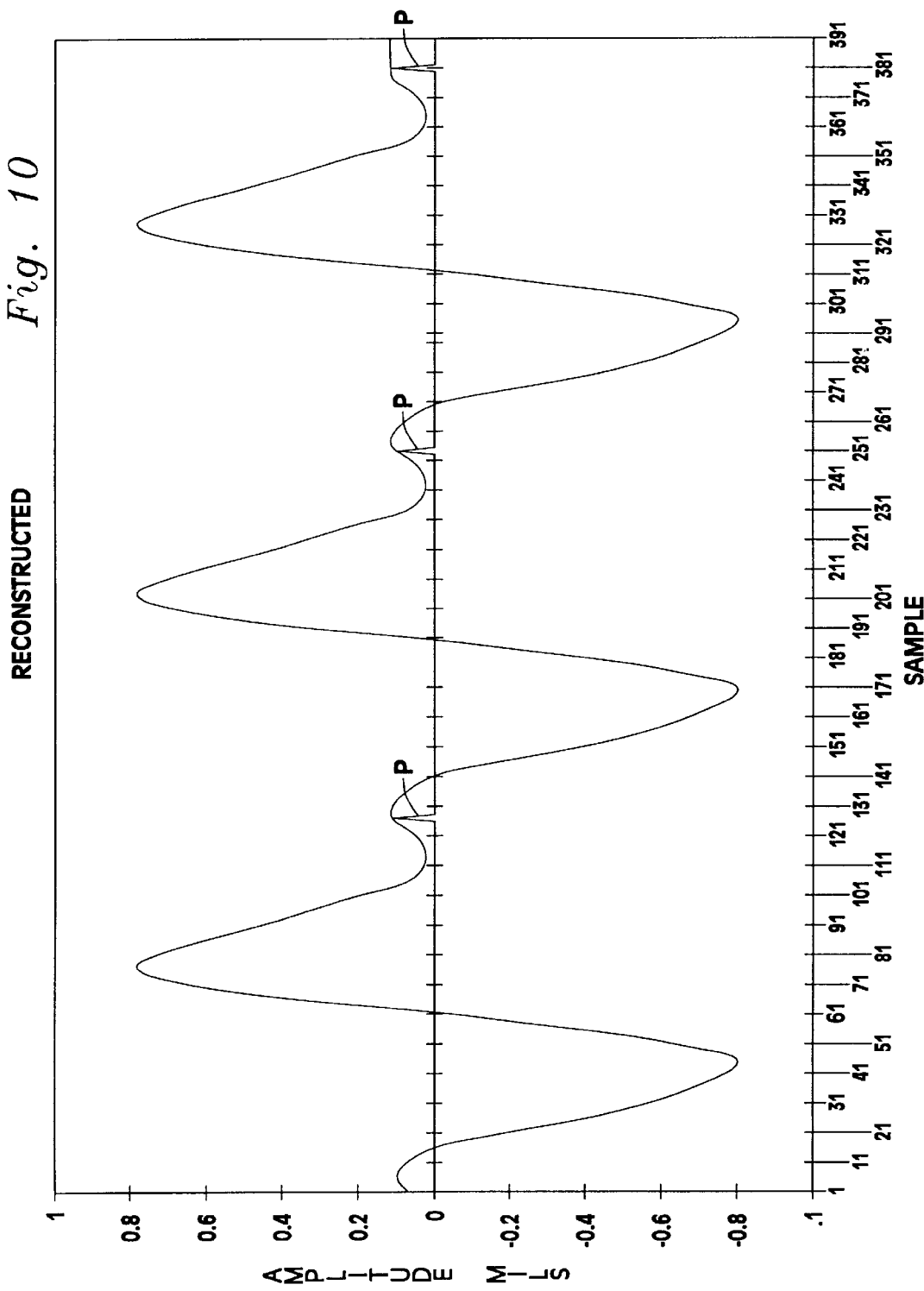
FIG. 10 is a graphical representation of the mechanical phase reference marks and continuous vibration signals reconstructed from the continuous vibration signals shown in FIG. 9 after being compressed according to the present invention.

FIGS. 11 and 12 respectively show uncompressed and compressed spectrum plots of the signals S and S' respectively shown in FIGS. 9 and 10. The compressed plot results from using the criteria of a fixed quantity of largest elements according to the invention. Specifically, FIG. 12 results in using twelve of the largest elements.

It will be appreciated that the machine data can be directly communicated from the sensors 21, 22, 24 to the remote computer 60 in order to perform the functions performed by the sampling means 30 and the computational means 40.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A signal processing method for processing machinery signals correlative to machine status, the steps including:
    sensing signals correlative to machine status;
    converting said signals into digital values;
    storing a series of said digital values into a packet defining a previously stored packet;
    comparing a subsequent packet of said digital values with said previously stored packet of said digital values;
    storing only said digital values included in said subsequent packet which are anomalous because they differ by a criteria from comparable digital values of said previously stored packet of said digital values;
    transmitting a signal correlative to said previously stored packet of digital values and to said subsequent packet of said digital values including flagging anomalous data in said subsequent packet of digital values.

2. The method of claim 1 further including the step of replacing corresponding digital values in said previously stored packet with the anomalous data from said subsequent packet for creating a new packet used for comparing further subsequent packets.

3. The method of claim 2 further including the step of indexing each packet of said digital values as they are stored and storing an indexing signature correlative with each said packet.

4. The method of claim 3 further including the step of transmitting said indexing signature when transmitting said signal correlative to said previously stored packet of digital values.

5. The method of claim 4 wherein said indexing signature includes information concerning the location of the digital values within each packet.

6. The method of claim 5 wherein said indexing signature includes the time of occurrence of the anomalous data.

7. The method of claim 6 wherein the step of sensing signals correlative to machine status includes sensing the signals at periodic intervals.

8. The method of claim 7 wherein the step of converting said signals into digital values further includes the steps of sampling said signals with a sampling means and transforming said signals into spectral elements via a fast fourier analysis algorithm.

9. A machine vibration signal processing method, the steps including:
    sampling a vibration signal;
    subjecting said vibration signal to a transformation means for transforming said vibration signal into a series of spectral elements;
    comparing said series of spectral elements against a criteria for retention and storing in a memory means said spectral elements which pass said criteria defining a previously stored series of spectral elements;
    sampling a subsequent vibration signal;
    subjecting said subsequent vibration signal to said transformation means for transforming said subsequent vibration signal into a subsequent series of spectral elements;
    comparing said subsequent series of spectral elements to said criteria for retention and then comparing said subsequent series of spectral elements which have passed said criteria for retention with said previously stored series of spectral elements;
    storing in said memory means spectral elements of said subsequent series which have passed said criteria for retention and which differ from said spectral elements of said previously stored series by a pre-determined amount.

10. The method of claim 9 including the step of reconstituting a continuous vibration signal from said stored spectral elements of said subsequent vibration signal and from all remaining spectral elements of said previous series which do not differ from said subsequent series by said pre-determined amount.

11. The method of claim 9 wherein the steps of sampling the vibration signal and sampling the subsequent vibration signal are both at a periodic interval.

12. The method of claim 11 further including the step of retaining both a magnitude value and a phase value for each spectral element stored in said memory means.

13. The method of claim 12 further including the step of indexing spectral elements which have passed said criteria for retention with a real-time of occurrence.

14. The method of claim 9 further including the step of re-comparing said spectral elements stored in said memory means with said criteria for retention and removing from said memory means said spectral elements which fail said criteria for retention.

15. An apparatus for compressing data correlative to continuous machine vibrations signals, comprising, in combination:
    at least one sensor operatively coupled to a machine for sensing machine vibration in the form of continuous electrical signals;
    sampling means adapted to receive from said at least one sensor continuous electrical signals and including means for converting into digital values said continuous electrical signals;
    a control circuit commanding said sampling means to convert said electrical signals into digital values;
    means for uniquely tagging each digital value with a real time value for identifying a time in history of an occurrence of when each instantaneous value of each continuous electrical signal correlative to each digital value was sensed by said at least one sensor;
    means for storing in a memory means a periodicity of said digital values;
    means for comparing at least one of said periodicity of said digital values with a subsequent periodicity of said digital values to determine anomalous digital values, and
    means for compressing data by storing in said memory means only said anomalous digital values of said subsequent periodicity of said digital values which have changed from at least one of said periodicity of said digital values.

16. A machine vibration signal processing method, the steps including:

sampling continuous vibration signals from a machine;

transforming said vibration signals into discrete digital values;

storing at least one packet of digital values in a memory means and storing a marker in said memory means for identifying the position and the time of capture of each digital value;

comparing a subsequent packet of digital values with at least one of said packet of digital values;

storing digital values of said subsequent packet of digital values which differ from at least one of said packet of digital values and storing markers for identifying the position and time of capture of each differing value;

comparing further subsequent packets of digital values with previously stored packets of digital values;

storing digital values of said further subsequent packets of digital values which differ from said previously stored values and storing markers in said memory means identifying the position and time of capture of each differing value;

reconstituting any stored packet of digital values into a continuous wave form from the values stored for said packet being reconstituted and from the values of at least one previously stored packet which correspond to values missing from said packet being reconstituted.

17. A signal compression method for storing historical data correlative to devolving machine status, the steps including:

sensing signals correlative to machine status;

sampling said signals;

transforming said sampled signals into a series of spectral elements defining a first reading;

determining dominant spectral components of a periodicity of said series of spectral elements based on a pre-determined criteria;

storing said periodicity of dominant spectral components defining a previously stored periodicity;

determining dominant spectral components of a subsequent periodicity of said series of spectral elements based on said pre-determined criteria;

comparing said subsequent periodicity of dominant spectral components with said previously stored periodicity of dominant spectral components to ascertain devolvement in respect of spectral components correlative to machine status;

compressing said subsequent periodicity of dominant spectral components by transmitting to and storing in a host computer said spectral components of said subsequent periodicity which change from said spectral components of said previously stored spectral components and when the changes occur;

defaulting to resensing in the absence of devolvement;

generating a continuous signal correlative to machine status by transforming said stored components of said subsequent periodicity and said stored components of said previously stored periodicity which fails to differ from said subsequent periodicity of dominant spectral components.

18. A method for compressing data from waveforms characterizing machine vibration, the steps including:

successively producing a series of samples representing generally instantaneous values of a series of waveforms at time-spaced intervals;

transforming a first period of said samples of a first waveform included in said series of waveforms into a first set of spectral elements;

storing only those elements in said first set of spectral elements which are significant based on a predetermined criteria;

transforming said series of samples of each subsequent waveform included in said series of waveforms into a series of subsequent sets of spectral elements;

compressing data by successively storing only those elements in a first subsequent set of spectral elements included in said series of subsequent sets of spectral elements which have changed since the last stored elements in said first set of spectral elements, and compressing data by successively storing only those elements in each said subsequent set of spectral elements following said first subsequent set which have changed since the last stored elements in said series of subsequent sets of spectral elements.

19. A method for compressing measurement data correlative to machine status, the steps including:

sensing machine data correlative to machine status;

sampling said data;

transforming said sampled data into spectral elements;

comparing said spectral elements to a user definable criteria for retention;

storing a series of said spectral elements which have passed said criteria for retention into a current interval of spectral elements;

comparing a subsequent series of said spectral elements which have passed said criteria for retention with said current interval of spectral elements;

compressing measurement data correlative to machine status by storing in a memory means those spectral elements from said subsequent series which have passed said user definable criteria for retention and which are anomalous because they differ by a user definable amount from comparable elements of said current interval of spectral elements.

20. The method of claim 19 wherein the step of comparing said spectral elements to a user definable criteria for retention includes the step of selecting a fixed quantity of largest spectral elements over a user definable period of spectral elements for the user definable criteria for retention.

21. The method of claim 19 wherein the step of comparing said spectral elements to the user definable criteria for retention includes selecting a percentage of the largest elements in a user definable period as the user definable criteria for retention.

22. The method of claim 19 wherein the step of sampling said data includes the step of sampling said data into discrete digital values synchronously with machine speed.

23. The method of claim 19 wherein the step of sampling said data includes the step of sampling said data into discrete values asynchronously with machine speed.

24. The method of claim 19 further including the step of sensing a mechanical phase angle of a rotating shaft of a machine in which data is being sensed and further including the step of creating a mechanical phase reference demarcation used to relate the mechanical phase angle of the rotating shaft to the sensed machine data correlative to machine status.

25. The method of claim 19 further including the step of sensing a mechanical phase reference mark and further including the step of demarcating the sensed machine data into periods having a length correlative to the sensed mechanical phase reference mark.

26. A method for compressing measurement data correlative to machine status, the steps including:

sensing machine data correlative to machine status;

sampling said data;

transforming said sampled data into spectral elements;

comparing said spectral elements to a user definable criteria for retention;

compressing measurement data correlative to machine status by storing in a memory means those spectral elements which have passed said user definable criteria for retention wherein said stored elements are correlative to machine status;

wherein the step of comparing said spectral elements with said user definable criteria for retention includes the steps of selecting a minimum element amplitude which is slightly larger than noise spectral amplitudes imbedded in the sensed machine data and retaining only those elements which have an amplitude greater than the user definable minimum element amplitude for reducing data volume and eliminating noise.

27. A method for compressing measurement data correlative to machine status, the steps including:

sensing machine data correlative to machine status;

sampling said data;

transforming said sampled data into spectral elements;

comparing said spectral elements to a user definable criteria for retention;

compressing measurement data correlative to machine status by storing in a memory means those spectral elements which have passed said user definable criteria for retention wherein said stored spectral elements are correlative to machine status;

further including the step of sensing a mechanical phase angle of a rotating shaft of a machine in which data is being sensed and further including the step of creating a mechanical phase reference demarcation used to relate the mechanical phase angle of the rotating shaft to the sensed machine data correlative to machine status;

wherein the step of sensing the mechanical phase angle includes the step of sensing a mechanical phase reference mark once per revolution of the shaft, and further including the step of demarcating the sensed machine data into periods having a length correlative to the sensed mechanical phase reference mark.

28. A method for compressing measurement data correlative to machine status, the steps including:

continuously sensing cyclic machine vibration from at least one machine in the form of electrical signals correlative to machine status;

sensing at least one mechanical phase reference mark on a rotating shaft of at least the one machine;

relating the at least one mechanical phase reference mark of the rotating shaft to the electrical signals of machine vibration wherein a mechanical angle defines intervals of electrical signals;

sampling the machine vibration electrical signals under the orchestration of a control signal;

transforming said sampled signals into spectral elements;

converting said spectral elements into intervals of amplitude and phase elements;

comparing both the amplitude and phase of each subsequent interval of amplitude and phase elements with a previous interval of amplitude and phase elements to determine if the amplitude and/or phase of each subsequent element has changed more than a user definable amount from the element of a previous interval;

communicating the changed elements to a remote site for compressing measurement data correlative to machine status by storing only the changed elements.

29. The method of claim 28 wherein the step of communicating the changed elements includes the step of communicating the changed elements via a radio frequency link.

30. The method of claim 28 wherein the step of communicating the changed elements includes the step of communicating the changed elements via an internet link.

31. The method of claim 28 wherein the step of communicating the changed elements includes the step of communicating the changed elements via a microwave link.

32. The method of claim 28 wherein the step of communicating the changed elements includes the step of communicating the changed elements via a satellite link.

33. The method of claim 28 wherein the step of communicating the changed elements includes the step of communicating the changed elements via a fiber optics link.

34. The method of claim 28 wherein the step of communicating the changed elements includes the step of communicating the changed elements via a direct wire link.

35. A device for compressing measurement data correlative to machine status, said device comprising in combination:

at least one sensor operatively coupled to a machine for sensing data correlative to machine status;

sampling means operatively coupled to said at least one sensor for sampling said sensed data into discrete elements;

processor means operatively coupled to said sampling means for transforming said discrete elements into spectral elements and converting said spectral elements into magnitude and phase elements;

means for defining intervals of the magnitude and phase elements;

means for storing a current interval of the magnitude and phase elements;

means for comparing a subsequent interval of magnitude and phase elements with said current interval of magnitude and phase elements;

means for storing only said elements from said subsequent interval which are anomalous because they differ by a criteria from comparable elements of said current interval of elements wherein compressed measurement data correlative to machine status is continuously captured.

36. The device of claim 35 further including means for replacing only those elements in said current interval which correspond to said anomalous elements from said subsequent interval to form a subsequent current interval of elements for future comparison by said comparing means.

37. A method for compressing measurement data correlative to machine status, the steps including:

sensing machine data correlative to machine status;

sampling said data;

transforming said sampled data into spectral elements;

comparing said spectral elements to a user definable criteria for retention;

compressing said sampled data by storing in a memory means those spectral elements which have passed said user definable criteria for retention wherein said stored spectral elements are correlative to machine status;

sensing a mechanical phase reference mark, and demarcating said sensed machine data into periods having a length correlative to said sensed mechanical phase reference mark.

38. A signal processing method for processing machinery signals correlative to machine status, the steps including:

sensing signals correlative to machine status;

converting said signals into digital values;

storing a series of said digital values into packets;

comparing a subsequent packet of said digital values with at least one said stored packet of said digital values;

storing said digital values included in said subsequent packet which are anomalous because they differ by a criteria from digital values of said at least one stored packet which has been compared with said subsequent packet;

transmitting a signal correlative to said subsequent packet of digital values including flagging anomalous data in said subsequent packet of digital values.

39. A signal processing method for processing machinery signals correlative to machine status, the steps including:

sensing data correlative to machine status;

sampling the data;

transforming the sampled data into periods of spectral elements;

storing a first period of the spectral elements in a memory defining a previous period of stored spectral elements;

comparing a subsequent period of spectral elements to the previous period for determining anomalous behavior between corresponding spectral elements;

using the anomalous spectral elements from the subsequent period to replace the corresponding spectral elements in the previous period for defining a new previous period of spectral elements.

40. The method of claim 39 further including the step of iteratively updating the new previous period of spectral elements by replacing spectral elements in the new previous period with any anomalous spectral elements determined each time further subsequent periods of spectral elements are compared with the new previous period of spectral elements.

41. The method of claim 39 further including the step of transmitting the first period of the spectral elements and the anomalous spectral elements of the subsequent period to a remote memory for storing the first period of the spectral elements and the anomalous spectral elements at identified positions of each respective period.

42. The method of claim 41 further including the step of iteratively updating the new previous period of spectral elements by replacing spectral elements in the new previous period with any anomalous spectral elements determined each time further subsequent periods of spectral elements are compared with the new previous period of spectral elements.

43. The method of claim 42 further including the step of transmitting to the remote memory anomalous spectral elements determined each time further subsequent periods of spectral elements are compared with the new previous period of spectral elements and storing the determined anomalous spectral elements at identified positions of each respective period.

44. The method of claim 43 further including the step of reconstituting any period of spectral elements by starting at a period of spectral elements that is to be reconstituted and sequencing backwards through the periods of spectral elements stored in the remote memory and using the spectral elements stored at identified positions in the periods which are different in position than the identified positions for the period being reconstituted.

45. A method for compressing data correlative to machine status, the steps including:

sensing data correlative to machine status;

sampling said data;

transforming said sampled data into a plurality of sets of spectral elements;

comparing a first set in the plurality of sets of spectral elements to a user definable criteria for retention;

storing in a memory those spectral elements which have passed the criteria for retention;

comparing a subsequent set of spectral elements in the plurality of sets of spectral elements to the criteria, and comparing those spectral elements which have passed the criteria for retention to the first set of spectral elements stored in memory compressing data by storing in the memory those spectral elements included in the subsequent set which are anomalous because they differ by a user definable amount from comparable elements of the first set of spectral elements stored in memory.

46. A signal processing method for processing machinery signals correlative to machine status, the steps including:

sensing data correlative to machine status;

sampling the data;

transforming the sampled data into periods of spectral elements;

storing a first period of the spectral elements in a memory defining a previous period of stored spectral elements;

comparing a subsequent period of spectral elements to the previous period of stored spectral elements for determining anomalous data between corresponding spectral elements;

transmitting a signal correlative to the subsequent period of spectral elements including flagging the anomalous data in the subsequent period of spectral elements.

* * * * *